(12) United States Patent
Robidoux

(10) Patent No.: US 6,177,565 B1
(45) Date of Patent: Jan. 23, 2001

(54) PROCESS FOR SYNTHESIZING PIPERAZIC ACID

(75) Inventor: Andrea L. C. Robidoux, Andover, MA (US)

(73) Assignee: Vertex Pharmaceuticals Inc., Cambridge, MA (US)

(\*) Notice: Under 35 U.S.C. 154(b), the term of this patent shall be extended for 0 days.

(21) Appl. No.: 09/235,894

(22) Filed: Jan. 22, 1999

Related U.S. Application Data

(63) Continuation-in-part of application No. 09/136,339, filed on Aug. 19, 1998.

(51) Int. Cl.[7] ............................................. C07D 231/04
(52) U.S. Cl. ...................................... 544/224; 540/567
(58) Field of Search ............................................. 544/224

(56) References Cited

U.S. PATENT DOCUMENTS 5,716,929  2/1998  Bemis et al. .

FOREIGN PATENT DOCUMENTS

| 98 05242 | 4/1998 | (FR) . |
|---|---|---|
| 98 05243 | 4/1998 | (FR) . |
| WO/93/23403 | 11/1993 | (WO) . |
| WO94/11353 | 5/1994 | (WO) . |
| WO95/35308 | 12/1995 | (WO) . |
| WO97/22619 | 6/1997 | (WO) . |
| 99/55724 | * 11/1999 | (WO) .................................. 544/224 |

OTHER PUBLICATIONS

M.R. Attwood et al., "The Design and Synthesis of the Angiotensin Converting Enzyme Inhibitor Cilazipril and Related Bicyclic Compounds", 1986, 1011–1019, J. Chem Soc Perkins Trans.

U. Schmidt et al., "Enantioselective Synthesis of (R) and (S)–Hexahydopyridazine–3–carboxylic Acid Derivatives", 223–229, Synthesis, 2, 1996.

\* cited by examiner

*Primary Examiner*—Robert Gerstl
(74) *Attorney, Agent, or Firm*—Andrew S. Marks; Ian Robert Silverman

(57) ABSTRACT

The invention relates to a process for synthesizing piperazic acid and similar, ring-containing acids. The invention also relates to a process for simultaneously N(2)-acylating piperazic acid or an ester thereof and forming a bicyclic ring structure. The invention also relates to the use of either or both processes in a method of synthesizing a bicyclic compound useful as an intermediate for the production of an inhibitor of a caspase, particularly an inhibitor of interleukin-1β converting enzyme ("ICE").

8 Claims, No Drawings

PROCESS FOR SYNTHESIZING PIPERAZIC ACID

CROSS-REFERENCE TO PRIOR APPLICATION

This application is a continuation-in-part of copending U.S. patent application Ser. No. 09/136,339, filed Aug. 19, 1998.

TECHNICAL FIELD OF THE INVENTION

The invention relates to a process for synthesizing piperazic acid and similar, ring-containing acids. The invention also relates to a process for simultaneously N(2)-acylating piperazic acid or an ester thereof and forming a bicyclic ring structure. The invention also relates to the use of either or both processes in a method of synthesizing a bicyclic compound useful as an intermediate for the production of an inhibitor of a caspase, particularly an inhibitor of interleukin-1β converting enzyme ("ICE").

BACKGOUND OF THE INVENTION

Piperazic acid derivatives are important intermediates in natural product synthesis and in the synthesis of biologically useful non-natural amino acids and peptidomimetics (e.g., inhibitors described in PCT publications WO 97/22619 and WO 95/35308). Several syntheses of piperazic acid and derivatives thereof have been described [Decicco et al., *Syn. Lett.*, p. 615 (1995); Schmidt et al., *Synthesis*, p. 223 (1996); Rutjes et al., *Tetrahedron*, p. 8605 (1993); PCT publications WO 97/22619 and WO 95/35308). In each case however, the synthesis requires multiple steps, utilizes expensive reagents and produces less than desirable yields.

Compounds containing a bicyclic, aza-containing ring systems have been prepared as conformationally restricted dipeptide surrogates for a variety of medically important compounds. In particular, such ring systems are present in angiotensin converting enzyme (ACE) inhibitors, such as Cilazapril®, and in caspase inhibitors, such as inhibitors of interleukin-1 converting enzyme (ICE).

Current methods for synthesizing compounds containing these byciclic aza-containing ring systems have many disadvantages. The typical methods of forming this ring system have been described [EP 94,095, WO 95/35308, WO 97/22619, U.S. Pat. Nos. 5,656,627, 5,716,929 and 5,756,486 and J. P. Kim, et al., *Tetrahedron Letters*, 38, pp. 4935–4938 (1997)].

These methods involve coupling an appropriately protected amino acid with the appropriately N(1)-protected piperazic acid or ester. After deprotection, the bicyclic system is then formed via an acid chloride coupling at the N(1) position.

The main disadvantages to such methods are the use of expensive reagents and the number of steps required for protection and deprotection making the overall process extremely time consuming. Moreover, these methods are often useful for research purposes but are not amenable to large scale production.

In order to be more commercially feasible, it would be desirable to produce compounds containing a byciclic aza-containing ring system in an easier, less expensive manner than has been previously described.

SUMMARY OF THE INVENTION

Applicant has solved the problems indicated above by providing: 1) a new method for synthesizing piperazic acid; and 2) a new method of simultaneously N(2)-acylating an N(1)-protected piperazic acid or an ester thereof and creating a bicyclic ring structure comprising that acylated piperazic acid or ester.

The first method involves treating a 1,4-dihaloalkyl ester with an N,N'-bis-protected hydrazine dissolved in DMF in the presence of a water scavenger, a metal hydroxide and a phase transfer catalyst. This method produces surprisingly increased yield of the desired protected piperazic acid.

The second method involves the formation of the desired bicyclic system in two, simple steps. This method also utilizes inexpensive reagents, does not require selective protection/deprotection, and is quite amenable to large scale production. Moreover, this method produces very little contaminating by-products. This method also preserves chirality between the N(1)-protected piperazic or similar acid or an ester thereof and the resulting byciclic aza-containing ring system.

This method is particularly useful for producing an intermediate that may be subsequently converted into a caspase inhibitor, particularly an inhibitor of ICE, through additional steps known in the art.

DETAILED DESCRIPTION OF THE INVENTION

Some of the abbreviations used throughout the specifications (including in chemical formulae) are:
Bu=butyl
Et=ethyl
Cbz=carboxybenzyl
DMF=N,N-dimethylformamide
THF=tetrahydrofuran
MTBE=methyl tert-butyl ether
DCC=dicyclohexyl carbodiimide
EDC=1-(3-Dimethylaminopropyl)-3-ethylcarbodiimide hydrochloride
Ac=acetyl.

According to one embodiment, the invention provides a process for producing compound E by reacting compounds C and D:

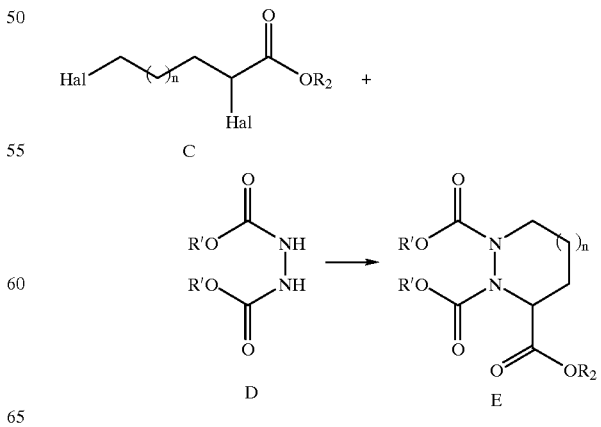

comprising the steps of:

a) dissolving compounds C and D together in DMF;
b) adding to said solution of C and D:
   i) a water scavenger;
   ii) a metal hydroxide selected from LiOH, NaOH or KOH; and
   iii) a phase transfer catalyst
c) allowing the mixture produced in step b) to react at room temperature for 2 to 48 hours;
d) adding an organic solvent and water to said mixture to create an aqueous phase and an organic phase; and
e) purifying compound E from said organic phase;

wherein:
$R_2$ is selected from hydrogen, C1–C6 straight or branched alkyl, C2–C6 straight or branched alkenyl or alkynyl or Ar, wherein said alkyl, alkenyl or alkynyl is optionally substituted with Ar;

n is 0 or 1;

"Hal" is any halogen; and each R' is an independently selected carboxyl protecting group The water scavenger referred to above may be selected from any water scavengers known in the art. These include, but are not limited to, $Na_2SO_4$, $MgSO_4$, and molecular sieves. Preferably, the water scavenger is sodium sulfate.

According to another preferred embodiment, the metal hydroxide used in the above method is LiOH.

The phase transfer catalyst referred to in the above method may also be selected from any such catalysts known in the art. These include, but are not limited to, $Bu_4NI$, Aliquat 336 (Aldrich Chemicals) and other quarternary ammonium salts. Preferably, the catalyst is $Bu_4NI$.

According to another preferred embodiment, n is 1.

According to yet another preferred embodiment, each Hal is Br.

In yet another preferred embodiment of the method set forth above, $R_2$ is t-butyl.

In another preferred embodiment, R' is benzyl.

According to another embodiment, the invention provides a process for converting compound G to compound H:

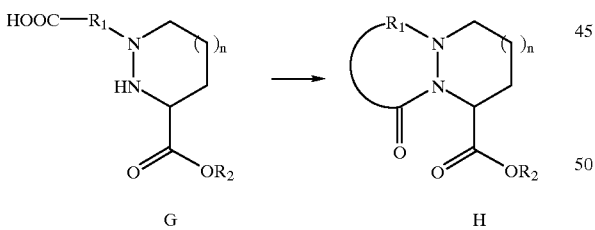

G          H wherein:
$R_1$ is a C2–C4 straight chain alkyl optionally substituted at any carbon with one or more substituents selected from C1–C6 straight or branched alkyl, C2–C6 straight or branched alkenyl or alkynyl, O—C1–C6 straight or branched alkyl, O—C2–C6 straight or branched alkenyl or alkynyl, oxo, halo, $NO_2$, $N(R_4)(R_4)$, CN, Ar or O—Ar;

$R_2$ is selected from hydrogen, C1–C6 straight or branched alkyl, C2–C6 straight or branched alkenyl or alkynyl or Ar, wherein said alkyl, alkenyl or alkynyl is optionally substituted with Ar;

n is 0 or 1;

Ar is a saturated, partially saturated or unsaturated monocyclic or bicyclic ring structure, wherein each ring contains 5 to 7 ring atoms and each ring optionally contains from 1 to 3 heteroatoms selected from O, N and S;

wherein Ar is optionally substituted at one or more ring atoms with one or more substituents independently selected from C1–C6 straight or branched alkyl, C2–C6 straight or branched alkenyl or alkynyl, O—C1–C6 straight or branched alkyl, O—C2–C6 straight or branched alkenyl or alkynyl, oxo, halo, $NO_2$, $N(R_4)(R_4)$, CN, $Ar_1$, O—$Ar_1$;

wherein $Ar_1$ is a saturated, partially saturated or unsaturated monocyclic or bicyclic ring structure, wherein each ring contains 5 to 7 ring atoms and each ring optionally contains from 1 to 3 heteroatoms selected from O, N and S; and each $R_4$ is independently selected from H or an amino protecting group, with the proviso that both $R_4$ are not simultaneously hydrogen.

The term "amino protecting group", as used herein, means a moiety that prevents chemical reactions from occurring on the nitrogen atom to which that protecting group is attached. An amino protecting group must also be removable by a chemical reaction.

In one preferred embodiment, $R_1$ is substituted at the terminal carbon bound to the —COOH moiety with a protected amine. The term "protected amine" as used herein, means a nitrogen-containing moiety which can be chemically modified to an amine.

In another preferred embodiment, $R_1$ is substituted at the other terminal carbon (i.e., the one bound to the ring nitrogen) with oxo, making $R_1$ an acyl-containing moiety. More preferred is when $R_1$ contains both the protected amine substituent and the oxo substituent. One of the most preferred $R_1$ groups is:

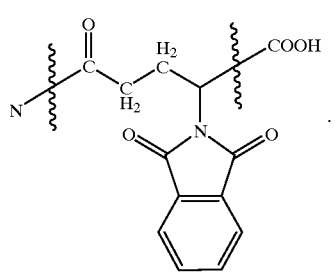

In another preferred embodiment, n is 1.

In yet another preferred embodiment, $R_2$ is t-butyl.

The method of this invention comprises the steps of:

(a) suspending compound G in an organic solvent selected from dichloroethane, dichloromethane, toluene, chlorobenzene, chloroform, monoglyme, diglyme or $CCl_4$;

(b) adjusting the temperature of the resulting solution to between 20° C. and 100° C.;

(c) adding base and more than about 1 equivalent of $RSO_pCl_p$ to said solution, wherein R is absent or is selected from C1–C6 straight or branched alkyl or Ar, and each p is independently 1 or 2; and (d) allowing the reaction to proceed over a period of between 2 and 24 hours.

Not all organic solvents may be used to dissolve compound G in step (a). The list of solvents set forth above are known to work. Other similar organic solvents may also work in the reaction and are to be considered part of the present invention. Preferably, the organic solvent is toluene or dichloroethane.

Step (b) is preferably carried out at about 70° C.

According to a alternate embodiment, in step (c), less than about 0.2 equivalents of N,N-dimethylformamide may also added.

In another preferred embodiment of step (c), $RSO_pCl_p$ is selected from methanesulfonyl chloride or $SOCl_2$. Preferably, in step (c), about 1 to 3 equivalents of $RSO_pCl_p$ are added.

According to yet another preferred embodiment of step (c), about 2 to 4 equivalents of base are added to the reaction. Preferably, the base is selected from pyridine, collidine, lutidine, $NaHCO_3$, imidazole, triethylamine, N-methylmorpholine, diisopropylethylamine or $K_2CO_3$. Most preferably, the base is 2,6-lutidine.

In step (c), the base and the $RSO_pCl_p$ are added simultaneously and may be added all at once to the reaction or gradually over period of time up to 3 hours.

Once the reaction is complete, we prefer to purify compound H by diluting the reaction with an organic solvent and then washing the solution first with $NaHCO_3$ and then with brine. The solution is then dried over $Na_2SO_4$ and concentrated.

Compound G may be obtained from compound E. That conversion may be achieved in one of two ways depicted below in Scheme 2, depending upon the nature of $R_1$.

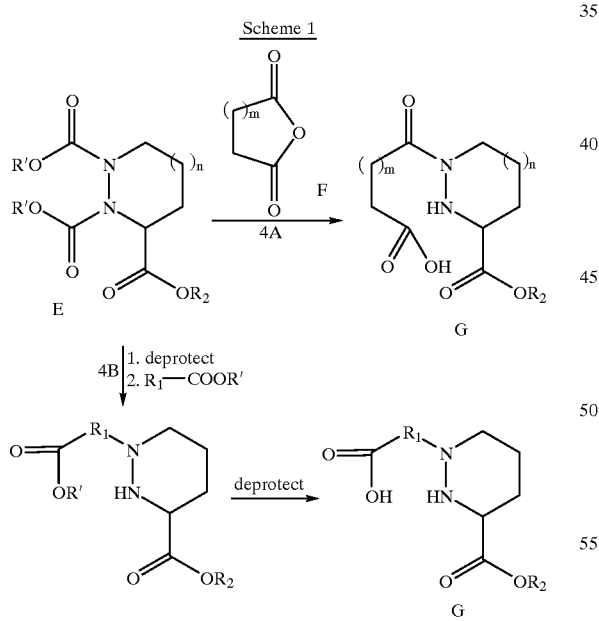

Scheme 1

In Scheme 1, m is 0, 1 or 2; and n, R', $R_1$ and $R_2$ are as defined above. Also, in compound F any of the unsubstituted ring carbon atoms may be optionally substituted by one or more substituents independently selected from C1–C6 straight or branched alkyl, C2–C6 straight or branched alkenyl or alkynyl, O—C1–C6 straight or branched alkyl, O—C2–C6 straight or branched alkenyl or alkynyl, oxo, $NO_2$, $N(R_4)(R_4)$, CN, Ar, or O—Ar, wherein said alkyl, alkenyl or alkynyl is optionally substituted with Ar, and wherein $R_4$ and Ar are as defined above.

Reaction 4A comprises stepwise deprotection and acylation (which can be performed in the same reaction vessel) if the carboxyl protecting groups can be removed by hydrogenolysis, (e.g., if the protecting group is benzyl) or utilizing transfer hydrogenation conditions. If not, a deprotection step must precede the addition of the anhydride for the acylation reaction.

In order to completely deprotect at both nitrogens under transfer hydrogenation conditions, at least 2 equivalents of the proton donor (e.g., $Et_3SiH$) must be added. If only one equivalent of the proton donor is added, deprotection occurs selectively at the N(2) nitrogen:

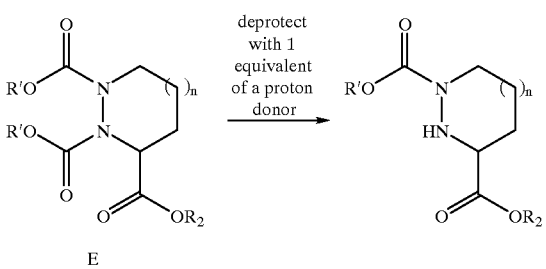

E

The resulting N(1) protected compound is also useful as an intermediate in producing medically important compounds, such as the ICE inhibitors described herein and in PCT publications WO 97/22619 and WO 95/35308. Thus, this reaction to produce an N(1) protected compound is also an embodiment of the present invention.

When compound F contains substituents and is not symmetrical, reaction 4A produces mixtures of compounds, wherein acylation of the N(1) nitrogen may occur at either C(O) functionality. This may be avoided by using substituents that favor the formation of the desired product. For example, in reaction 4A, the use of:

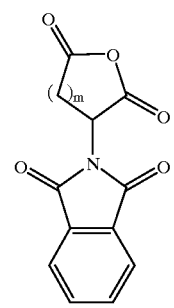

as compound F forces the formation of a compound wherein acylation of the N(1) nitrogen occurs at the C(O) functionality furthest away from the pthalimide substituent.

In order to avoid an unwanted reaction at the N(2) nitrogen in step 4B, the two carboxy protecting groups (R') on compound E should be different, such that the N(1) protecting group (—COOR') can be selectively removed without removing the N(2) protecting group.

The creation of intermediate E can be achieved by standard syntheses known in the art. More preferably, intermediate E is synthesized by reacting compounds C and D according to the method of this invention as set forth above.

Intermediate compound G containing the protected amine on $R_1$, and its subsequent conversion to compound H, may serve as the key intermediate and synthesis step, respectively, in an improvement in the synthesis of known caspase inhibitors, particularly inhibitors of interleukin-1 converting enzyme ("ICE"), such as those described in U.S. Pat. Nos. 5,716,929, 5,656,627, and 5,756,466 and in PCT publications WO 95/35308 and WO 97/22619.

Those inhibitors have the general formula (I):

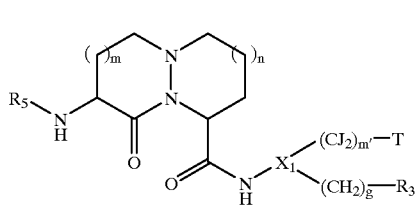

(I)

wherein:
  any ring is optionally substituted at any carbon by $Q_1$, at any nitrogen by $R_5$, and at any atom by =O, —OH, —COOH, or halogen;
  $X_1$ is CH or N;
  g is 0 or 1;
  m and m' are independently 0, 1 or 2;
  n is 0 or 1;
  each J is independently selected from —H, —OH, or —F, provided that when a first and a second J are bound to a C, and said first J is —OH, then said second J is —H;
  T is —$Ar_3$, —OH, —$CF_3$, —C(O)—C(O)—OH, —C(O)—OH or any biosteric replacement for —C(O)—OH;
  $R_3$ is —CN, —CH=CH—$R_9$, CH=N—O—$R_9$, —$(CH_2)_{1-3}$—$T_1$—$R_9$, —$CJ_2$—$R_9$, —C(O)—$R_{13}$, or —C(O)—C(O)—N($R_5$)($R_{10}$);
  $T_1$ is —CH=CH—, —O—, —S—, —SO—, —$SO_2$—, —$NR_{10}$—, —$NR_{10}$—C(O)—, —C(O)—, —O—C(O)—, —C(O)—O—, —C(O)—$NR_{10}$—, O—C(O)—$NR_{10}$—, —$NR_{10}$—C(O)—O—, —$NR_{10}$—C(O)—$NR_{10}$—, —$S(O)_2$—$NR_{10}$—, —$NR_{10}$—S$(O)_2$— or —$NR_{10}$—$S(O)_2$—$NR_{10}$—;
  each $R_5$ is independently selected from —H, —$Ar_1$, —C(O)—$Ar_1$, —$S(O)_2$—$Ar_1$, —$R_9$, —C(O)—$NH_2$, —$S(O)_2$—$NH_2$, —C(O)—$R_9$, —C(O)—O—$R_9$, —$S(O)_2$—$R_9$, —C(O)—N($R_{10}$)($Ar_1$), —$S(O)_2$—N ($R_{10}$)($Ar_1$), —C(O)—N($R_{10}$)($R_9$), or —$S(O)_2$—N ($R_{10}$)($R_9$);
  each $R_9$ is a $C_{1-6}$ straight or branched alkyl group optionally singly or multiply substituted with —OH, —F, =O or $Ar_1$, wherein any $R_9$ may be substituted with a maximum of two $Ar_1$;
  each $R_{10}$ is independently selected from —H or $C_{1-6}$ straight or branched alkyl;
  $R_{13}$ is —H, —$Ar_1$, —$R_9$, —$T_1$—$R_9$ or —$(CH_2)_{1-3}$—$T_1$—$R_9$;
  each $Ar_1$ is a cyclic group independently selected from a monocyclic, bicyclic or tricyclic aryl group containing 6, 10, 12 or 14 carbon atoms; a monocyclic, bicyclic or tricyclic cycloalkyl group containing between 3 and 15 carbon atoms, said cycloalkyl group being optionally benzofused; or a monocyclic, bicyclic or tricyclic heterocycle group containing between 5 and 15 ring atoms and at least one heteroatom group selected from —O—, —S—, —SO—, —$SO_2$—, =N—, or —NH—, wherein said heterocycle group optionally contains one or more double bonds and optionally comprises one or more aromatic rings;

$Ar_3$ is a cyclic group selected from phenyl, a 5-membered heteroaromatic ring or a 6-membered heteroaromatic ring, wherein said heteroaromatic rings comprise from 1-3 heteroatom groups selected from —O—, —S—, —SO—, —$SO_2$—, =N—, or —NH—;

wherein each $Ar_1$ or $Ar_3$ is optionally singly or multiply substituted at any ring atom by —$NH_2$, —C(O)—OH, —Cl, —F, —Br, —I, —$NO_2$, —CN, =O, —OH, -perfluoro $C_{1-3}$ alkyl,

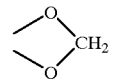

or —$Q_1$; and each $Q_1$ is independently selected from —$Ar_1$, —$R_9$, —$T_1$—$R_9$, or $(CH_2)_{1-3}$—$T_1$—$R_9$; provided that when —$Ar_1$ is substituted with a $Q_1$ which comprises one or more additional —$Ar_1$ groups, said additional —$Ar_1$ groups are not substituted with $Q_1$.

Preferably, the process of this invention is used as a step in the synthesis of a compound of formula I, wherein n is 1 and m is 2.

In another preferred embodiment, the process of this invention is used as a step in the synthesis of a compound of formula I, wherein $R_5$ is an acyl moiety selected from —C(O)—$Ar_1$, —C(O)—$NH_2$, —C(O)—$R_9$, —C(O)—O—$R_9$, —C(O)—N($R_{10}$)($Ar_1$), or —C(O)—N($R_{10}$)($R_9$).

In yet another preferred embodiment, the process of this invention is used as a step in the synthesis of a compound of formula I, wherein $X_1$ is CH; each J is H; m' is 1; T is —COOH or a biosteric replacement for —COOH; g is 0; and $R_3$ is —C(O)—$R_{13}$.

In the most preferred embodiment of using the process of this invention as a step in the synthesis of a compound of formula I, said compound has the structure:

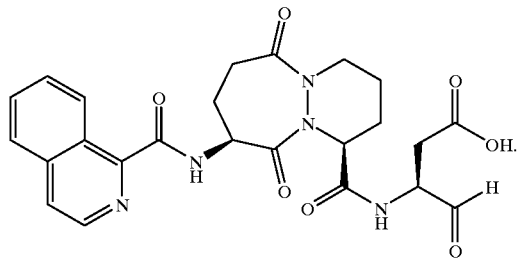

Alternatively, the process of this invention may be used as a step in the synthesis of a compound of the formula (II):

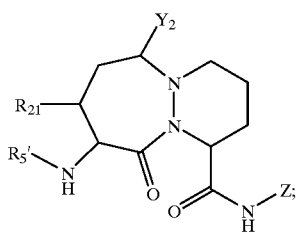

wherein:

Z is selected from

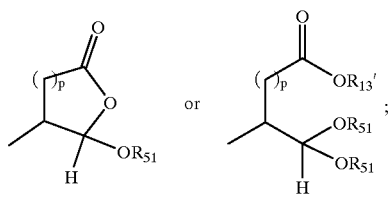

p is 1 or 2;

each $R_{5'}$ is independently selected from —C(O)—$R_{10'}$, —C(O)O—$R_{9'}$, —C(O)—N($R_{10'}$)($R_{10'}$)—S(O)$_2$—$R_{9'}$, —S(O)$_2$—NH—$R_{10'}$, —C(O)—CH$_2$—O—$R_{9'}$, —C(O)C(O)—$R_{10'}$, —$R_{9'}$, —H, —C(O)C(O)—O$R_{10'}$, or —C(O)C(O)—N($R_{9'}$)($R_{10'}$);

each $R_{9'}$ is independently selected from —$Ar_1$ or a —$C_{1-6}$ straight or branched alkyl group optionally substituted with $Ar_1$, wherein the —$C_{1-6}$ alkyl group is optionally unsaturated;

each $R_{10'}$ is independently selected from —H, —$Ar_1$, a —$C_{3-6}$ cycloalkyl group, or a —$C_{1-6}$ straight or branched alkyl group optionally substituted with $Ar_{3'}$, wherein the —$C_{1-6}$ alkyl group is optionally unsaturated;

$R_{13'}$ is selected from H, $Ar_1$, or a $C_{1-6}$ straight or branched alkyl group optionally substituted with $Ar_1$, —CONH$_2$, —O$R_{5'}$, —OH, —O$R_{9'}$, or —CO$_2$H;

each $R_{51}$ is independently selected from $R_{9'}$, —C(O)—$R_{9'}$, —C(O)—N(H)—$R_{9'}$, or two $R_{51}$ taken together form a saturated 4–8 member carbocyclic ring or heterocyclic ring containing —O—, —S—, or —NH—;

each $R_{21}$ is independently selected from —H or a —$C_{1-6}$ straight or branched alkyl group;

$Y_2$ is —H$_2$ or =O each $Ar_1$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, SO$_2$, =N—, and —NH—, said heterocycle group optionally containing one or more double bonds, said heterocycle group optionally comprising one or more aromatic rings, and said cyclic group optionally being singly or multiply substituted by —$Q_1$;

each $Q_1$ is independently selected from the group consisting of —NH$_2$, —CO$_2$H, —Cl, —F, —Br, —I, —NO$_2$, —CN, =O, —OH, -perfluoro $C_{1-3}$ alkyl, $R_{5'}$, —O$R_{5'}$, —NH$R_{5'}$, O$R_{9'}$, —N ($R_{9'}$)($R_{10'}$), $R_{9'}$, —C(O)—$R_{10'}$, and

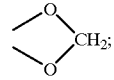

provided that when —$Ar_1$ is substituted with a $Q_1$ group which comprises one or more additional —$Ar_1$ groups, said additional —$Ar_1$ groups are not substituted with another —$Ar_1$.

Preferably, the process of this invention is used as a step in the synthesis of a compound of formula II, wherein $Y_2$ is O and $R_{21}$ is H.

In another preferred embodiment, the process of this invention is used as a step in the synthesis of a compound of formula II, wherein $R_{5'}$ is selected from —C(O)—$R_{10'}$, —C(O)O—$R_{9'}$, —C(O)—N($R_{10'}$)($R_{10'}$), —C(O)—CH$_2$—O—$R_{9'}$, —C(O)C(O)—$R_{10'}$, —C(O)C(O)—O$R_{10'}$, or —C(O)C(O)—N($R_{9'}$)($R_{10'}$).

In yet another preferred embodiment, the process of this invention is used as a step in the synthesis of a compound of formula II, wherein Z is

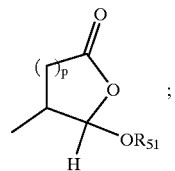

p is 1 and $R_{51}$ is selected from —$Ar_1$, —$C_{1-6}$ straight or branched alkyl or —$C_{1-6}$ straight or branched alkyl substituted with $Ar_1$.

In the most preferred embodiment of using the process of this invention as a step in the synthesis of a compound of formula II, said compound has the structure:

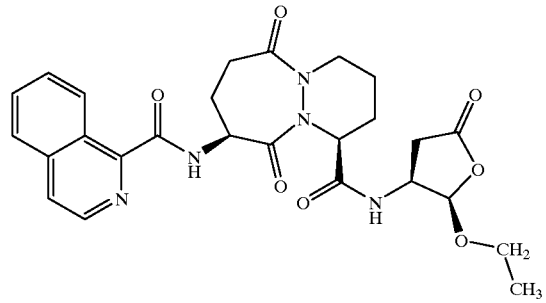

In the synthesis of these inhibitors, the terminal carbon of $R_1$ adjacent the —COOH moiety contains a protecting substituent. Preferably that protecting substituent is

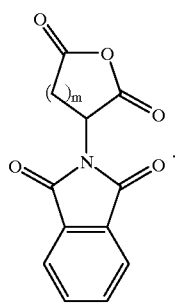

The synthesis steps from compound H to the inhibitors set forth above involve removal of the protecting substituent on $R_1$; coupling of the $R_5$—NH— or $R_{5'}$—NH— moiety in its place; hydrolysis of the $R_2$ group; and coupling of the amine

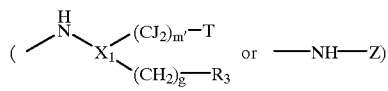

in its place;.

The removal of the protecting substituent on $R_1$ is typically carried out with hydrazine. The subsequent coupling of the resulting amine to form the $R_5$—NH— or $R_{5'}$—NH— moiety is achieved with standard coupling reagents, such as EDC, DCC or acid chloride.

Depending upon the nature of $R_2$, its hydrolysis may be achieved with an acid (when $R_2$ is t-butyl), a hydroxide (when $R_2$ is any other alkyl, alkenyl or alkynyl or Ar) or hydrogenolysis (when $R_2$ is an Ar-substituted alkyl, alkenyl or alkynyl). This produces the corresponding acid from the ester.

The acid is then coupled to the amine with standard coupling reagents, such as EDC, DCC or acid chloride.

In order that this invention be more fully understood, the following examples are set forth. These examples are for the purpose of illustration only and are not to be construed as limiting the scope of the invention in any way.

EXAMPLE 1

Synthesis of a 7,6 Scaffold for a Caspase Inhibitor

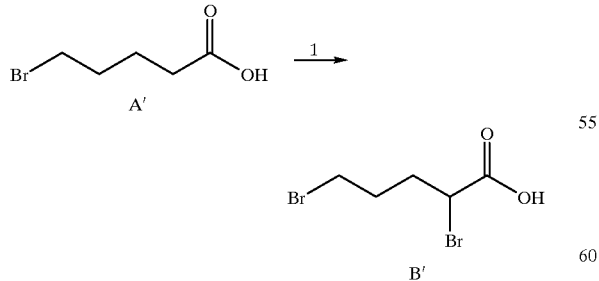

Compound A' was dissolved in 5 equivalents of $SOCl_2$ and then heated to 80° C. for 1 hour. The solution was then cooled to 50° C. and 2 equivalents of bromine were added. The solution was incubated at 50° C. for an additional 12 hours until the red color disappeared. We then cooled the solution to 10° C. and added 4 volumes of water. The solution was then re-heated to 50° C. for another hour. We then separated the organic and aqueous layer, washed the organic layer consecutively with water, $Na_2SO_3$ and then brine, removing the aqueous layer after each washing. The final organic layer was then isolated, dried over $Na_2SO_4$ and concentrated to produce compound B' as an amber oil.

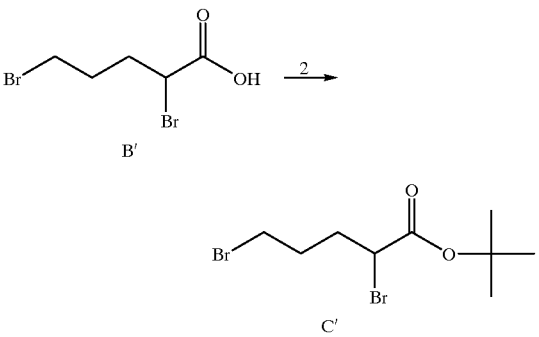

Compound B' was treated with 1 equivalent of tert-butanol and 0.1 equivalents of 4-(dimethylamino)pyridine in a solution of and the resulting solution cooled to 7° C. We then added a solution of 1 equivalent of DCC in toluene while maintaining reaction temperature at less than 22° C. The cooling bath was removed and the reaction was stirred at ambient temperature under a nitrogen atmosphere for 16 hours. The reaction mixture was then diluted with hexane and cooled to 9° C. The resulting solids were removed by filtration. The filtrate was washed consecutively with 0.1N HCl, water, and then sodium bicarbonate. The filtrate was then dried over sodium sulfate and concentrated in vacuo to afford compound C' as a yellow oil.

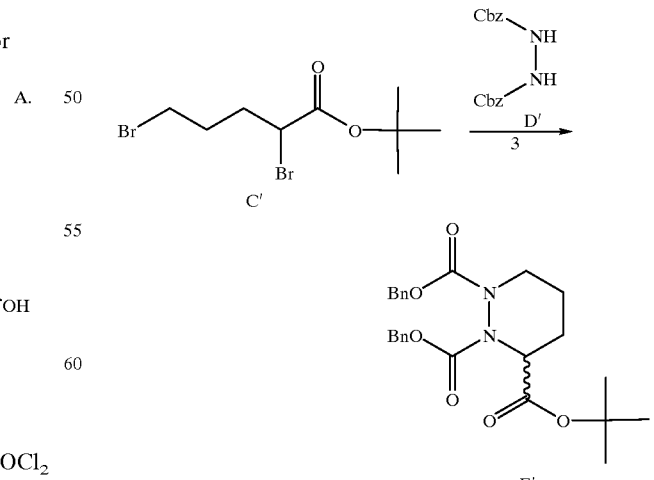

Compound D' was combined with 1.2 equivalents of compound C' and dissolved in DMF at ambient temperature under nitrogen atmosphere. We then added granular sodium sulfate, 2.5 equivalents of LiOH monohydrate, and then 0.1 equivalents Bu$_4$NI to the resulting solution. The reaction temperature was maintained at between 20° C. and 30° C. and allowed to stir for 16 hours. The reaction mixture was then diluted with ethyl acetate and water and the layers separated. The organic layer was washed with water and then brine, dried over sodium sulfate and concentrated in vacuo to produce an amber oil. This oil was then dissolved in 5 volumes of ethanol at ambient temperature. We then added 2.5 volumes of water. The resulting mixture was allowed to stir until a white solid formed (approximately 5 hours). The crystallized product was isolated via filtration then dried in vacuo to afford compound E' as a white solid.

D.

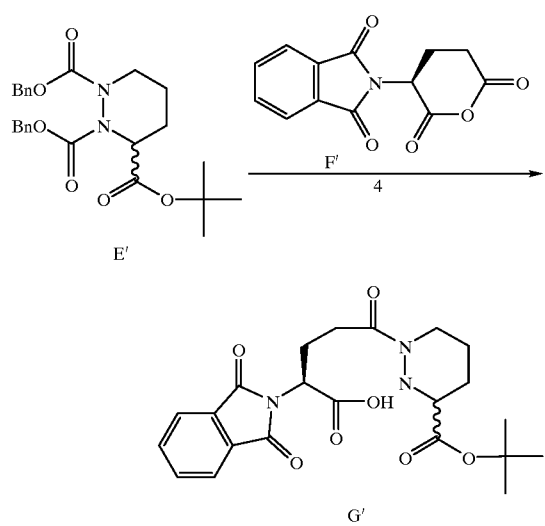

We dissolved compound E' in THF. We then added, at ambient temperature under a nitrogen atmosphere, 0.02 equivalents of triethylamine and 0.01 equivalents of Pd(OAc)$_2$. A solution of 2.5 equivalents of triethylsilane (Et$_3$SiH) in THF was then added and the resulting black solution was allowed to stir for 16 hours to complete the reaction. We then added a saturated, aqueous solution of sodium bicarbonate followed by a solution of compound F' in THF. After 30 minutes, the layers were separated and the aqueous layer acidified to pH 4.5 with aqueous citric acid. The product in the aqueous layer was then extracted into ethyl acetate. The organic layer was isolated, washed with brine, dried over sodium sulfate and concentrated in vacuo to produce a white foam. This crude product was then recrystallized from MTBE to afford compound G' as a white powder.

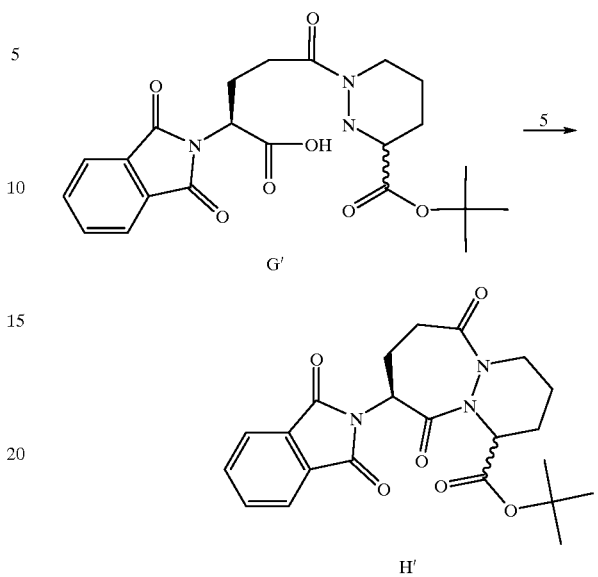

Method #1:

To a suspension of compound G' and 0.1 equivalents of DMF in dichloroethane, at 70° C. we added 5 equivalents of 2,6-lutidine simultaneously with 2.5 equivalents of SOCl$_2$ over a period of 3 hours. The reaction was then diluted with toluene and washed consecutively with NaHCO$_3$ and brine. The solution was then dried over Na$_2$SO$_4$ and concentrated in vacuo to afford compound H' as a yellow solid.

Method #2:

To a suspension of compound G' in dichloroethane, at 70° C., we added 4 equivalents of 2,6-lutidine followed by 2 equivalents of methanesulfonyl chloride. The resulting solution was stirred at 70° C. for 12 hours. The reaction was then diluted with toluene and washed consecutively with NaHCO$_3$ and brine. The solution was then dried over Na$_2$SO$_4$ and concentrated in vacuo to afford compound H' as a white solid. Method #2 produced a significantly higher yield of H' as compared to Method, #1.

EXAMPLE 2

Use of Intermediate H' to Produce an Inhibitor of ICE

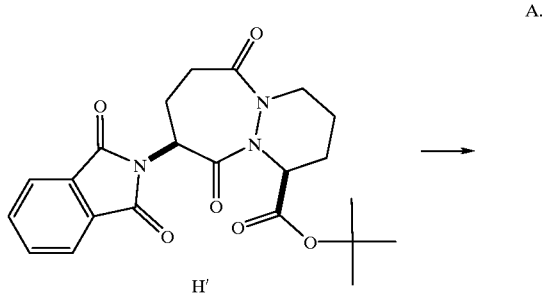

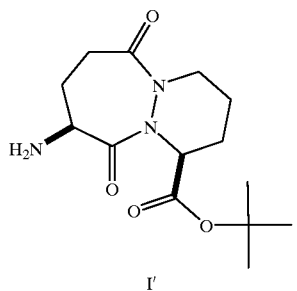

I' t-Butyl-9-amino-6, 10-dioxo-1,2,3,4,7,8,9,10-octahydro-6-H-pyridazino[1,2-a][1,2] diazepine-1-carboxylate (GB 2,128,984)

To a suspension of H' (107 g, 0.25 mol) in ethanol (900 mL) was added hydrazine (27 mL, 0.55 mol) and the resulting mixture was allowed to stir at ambient temperature. After 4 hours, the reaction was concentrated in vacuo and the resulting white solid was suspended in acetic acid (1 L of 2N) and allowed to stir at ambient temperature for 16 hours. The resulting white solid was filtered off and washed with water. The filtrate was made basic by the addition of solid sodium carbonate and the product extracted with dichloromethane. The organic layer was washed with brine, dried over magnesium sulfate and concentrated in vacuo to afford 79 mg of compound I' as a yellow viscous oil.

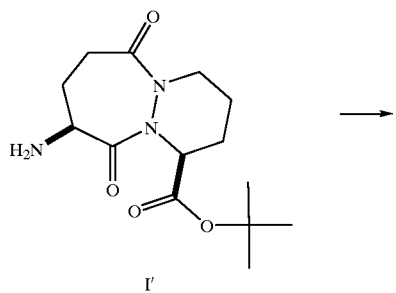

I'

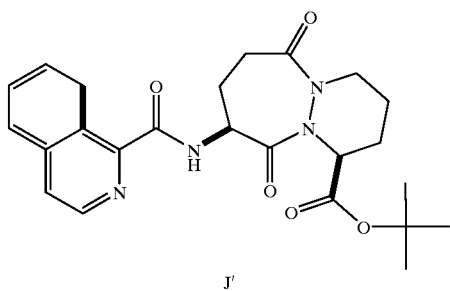

J' t-Butyl-9-(isoquinolin-1-oylamino)-6, 10-dioxo-1,2,3,4,7,8,9,10-octahydro-6-H-pyridazino[1,2-a][1,2] diazepine-1-carboxylate To a solution of the amine I' (79 g, 0.265 mol) and isoquinolin-1-carboxylic acid (56 g, 0.32 mol) in dichloromethane:DMF (400 mL:400 mL) was added hydroxybenzotriazole (54 g, 0.4 mol) and 1-(3-dimethylaminopropyl)-3-ethylcarbodiimide hydrochloride (74 g, 0.39 mol) and the resulting mixture was allowed to stir at ambient temperature for 16 hours. The reaction mixture was poured into water and extracted with ethyl acetate. The ethyl acetate layer was washed with 0.5N sodium bisulfate, water, sodium bicarbonate, brine, dried over sodium sulfate and concentrated in vacuo to afford 122 g of compound J' as an orange solid-foam.

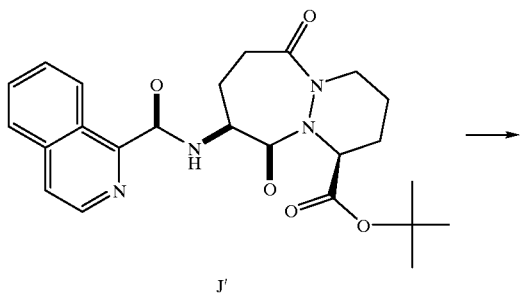

J'

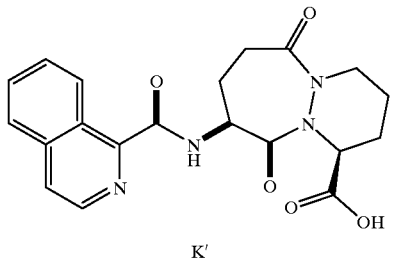

K'

9-(isoquinolin-1-oylamino)-6, 10-dioxo-1,2,3,4,7,8,9,10-octahydro-6-H-pyridazino[1,2-a][1,2] diazepine-1-carboxylic acid A solution of the ester J' (122 g) in dichloromethane and trifluoroacetic acid (200 mL) was allowed to stir at ambient temperature for 16 hours. The reaction mixture was concentrated to a black oil which was then triturated with acetonitrile and ether to afford 98 g of compound K' as a pale yellow solid.

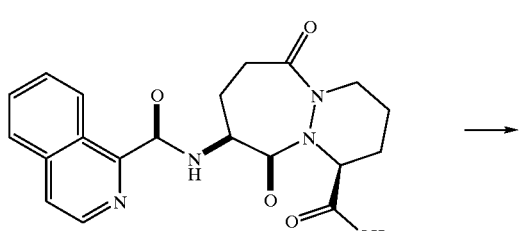

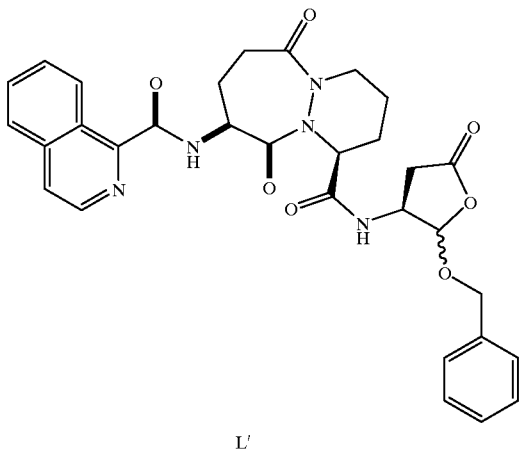

L'

[1S, 9S (2RS, 3S)] N-(2-benzyloxy-5-oxotetrahydrofuran-3-yl)-6,10-dioxo-9-(isoquinolin-1-oylamino)-1,2,3,4,7,8,9,10-octahydro-6-H-pyridazino[1,2-a][1,2] diazepine-1-carboxamide To a solution of (3S, 2RS) 3-allyloxycarbonylamino-2-(benzyl)oxy-5-oxotetrahydrofuran [*Bioorg. & Med. Chem. Lett.*, 2, pp. 615–618 (1992)] (4.4 g, 15.1 mmol) in dichloromethane was added N,N-dimethylbarbituric acid (5.9 g, 3.8 mmol) then tetrakispalladium(0) triphenyl phosphine (1.7 g, 1.5 mmol) and the resulting mixture was allowed to stir at ambient temperature for 15 minutes. To the resulting mixture was added the acid, compound K' (5.0 g, 12.6 mmol), hydroxybenzotriazole (2.0 g, 14.8 mmol) then and 1-(3-dimethylaminopropyl)-3-ethylcarbodiimide hydrochloride (2.7 g, 14 mmol) and the reaction was allowed to stir for 3 hours at ambient temperature. The reaction mixture was then poured into water and extracted with ethyl acetate. The organics were washed with 0.5M sodium bisulfate, water, sodium bicarbonate, brine, dried over magnesium sulfate and concentrated in vacuo to afford 2.6 g of the crude product as a yellow foam. The crude material was purified by column chromatography (SiO$_2$, dichloromethane:acetone 9:1–3:1) to afford 1.2 g of the compound L'.

Compound L' and related compounds that may be synthesized using the method of this invention as an intermediate step are described in WO 97/22619, the disclosure of which is herein incorporated by reference. Those related compounds may be synthesized from the product of the method of this invention, H or H', through modifications of the procedure set forth in Example 2. Such modifications are well known in the art.

While we have hereinbefore presented a number of embodiments of this invention, it is apparent that my basic construction can be altered to provide other embodiments which utilize the methods of this invention. Therefore, it will be appreciated that the scope of this invention is to be defined by the claims appended hereto rather than the specific embodiments which have been presented hereinbefore by way of example.

We claim:

1. A process for producing compound E by reacting compounds C and D:

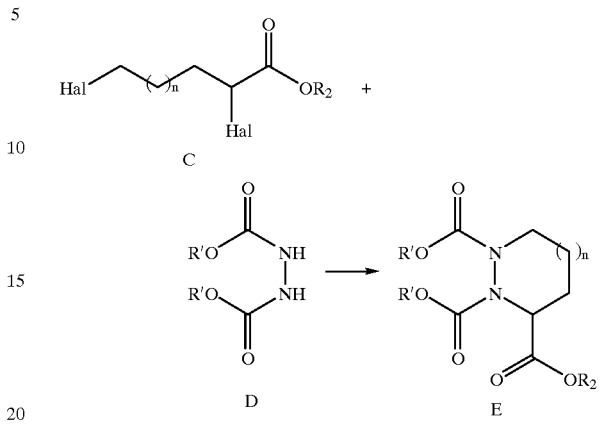

comprising the steps of:
a) dissolving compounds C and D together in DMF;
b) adding to said solution of C and D:
  i) a water scavenger;
  ii) a metal hydroxide selected from LiOH, NaOH or KOH; and
  iii) a phase transfer catalyst
c) allowing the mixture produced in step b) to react at room temperature for 2 to 48 hours;
d) adding an organic solvent and water to said mixture to create an aqueous phase and an organic phase; and
e) purifying compound E from said organic phase;
wherein:

$R_2$ is selected from hydrogen, C1–C6 straight or branched alkyl, C2–C6 straight or branched alkenyl or alkynyl or Ar, wherein said alkyl, alkenyl or alkynyl is optionally substituted with Ar;

n is 0 or 1;

"Hal" is any halogen; and each R' is an independently selected carboxyl protecting group.

2. The process according to claim 1, wherein said water scavenger is sodium sulfate.

3. The process according to claim 1, wherein said metal hydroxide is LiOH.

4. The process according to claim 1, wherein said phase transfer catalyst is Bu$_4$NI.

5. The process according to claim 1, wherein n is 1.

6. The process according to claim 1, wherein each Hal is Br.

7. The process according to claim 1, wherein $R_2$ is t-butyl.

8. The process according to claim 1, wherein R' is benzyl.

* * * * *